United States Patent
Torai

[11] Patent Number: 6,130,438
[45] Date of Patent: Oct. 10, 2000

[54] WRAPPING PAPER DEFECT INSPECTION APPARATUS FOR A CIGARETTE MANUFACTURING MACHINE

[75] Inventor: Hiroyuki Torai, Tokyo, Japan

[73] Assignee: Japan Tobacco Inc., Tokyo, Japan

[21] Appl. No.: 09/134,875

[22] Filed: Aug. 17, 1998

[30] Foreign Application Priority Data

Aug. 20, 1997 [JP] Japan ..................................... 9-223563

[51] Int. Cl.$^7$ ........................ G01N 21/894; A24C 5/345
[52] U.S. Cl. ................. 250/559.46; 250/559.15; 250/559.24; 250/559.27; 250/559.42; 131/906; 131/907
[58] Field of Search ................................ 250/221, 222.1, 250/223 R, 224, 559.03, 559.12, 559.15, 559.2, 559.24, 559.27, 559.39, 559.4, 559.42, 559.45, 559.46; 209/535, 536; 131/58, 60, 65, 906, 907

[56] References Cited

U.S. PATENT DOCUMENTS

| | | | |
|---|---|---|---|
| 4,135,344 | 1/1979 | Seragnoli | 209/535 |
| 4,537,206 | 8/1985 | Lorenzen et al. | |
| 4,563,228 | 1/1986 | Luders et al. | |
| 4,972,494 | 11/1990 | White et al. | 209/535 |
| 5,341,824 | 8/1994 | Fletcher et al. | |
| 5,476,108 | 12/1995 | Dominguez et al. | 131/108 |
| 5,746,225 | 5/1998 | Okumoto et al. | 131/84.1 |
| 5,944,278 | 8/1999 | Stevens, III et al. | 242/525.4 |

Primary Examiner—John R Lee
Attorney, Agent, or Firm—Birch, Stewart, Kolasch & Birch LLP

[57] ABSTRACT

A wrapping paper defect inspection apparatus for a cigarette manufacturing machine is provided which permits easy and reliable detection of a defect, such as a pinhole, in elongate wrapping paper continuously transported at high speed and which is suited for rejecting without fail cigarettes formed using a defective portion of the wrapping paper. Optical sensors are arranged at a transportation path of the wrapping paper for detecting transmission of light irradiated onto a region of the wrapping paper excluding the edge portions thereof, and a defect in the wrapping paper, such as a pinhole, is detected in accordance with whether or not the optical sensors have received light. Further, a pair of auxiliary optical sensors are provided for detecting transmission of light irradiated to regions including the respective edge portions of the wrapping paper, and based on the sum of amounts of light received by the auxiliary optical sensors, a defective or narrower portion of the wrapping paper than a prescribed width is detected. The result of defect detection is output in synchronism with the timing for wrapping shredded tobacco in the wrapping paper, to reject defective cigarettes.

6 Claims, 3 Drawing Sheets

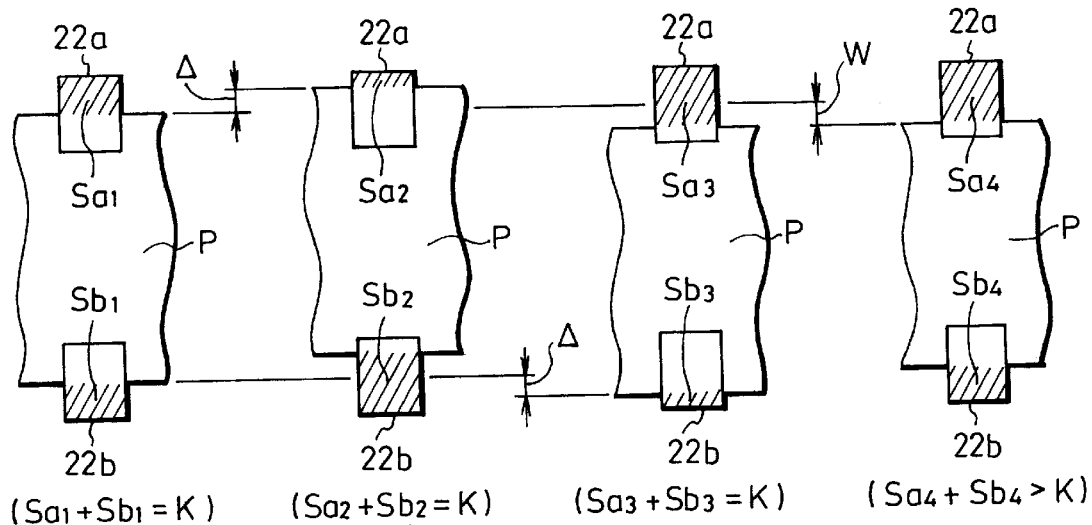
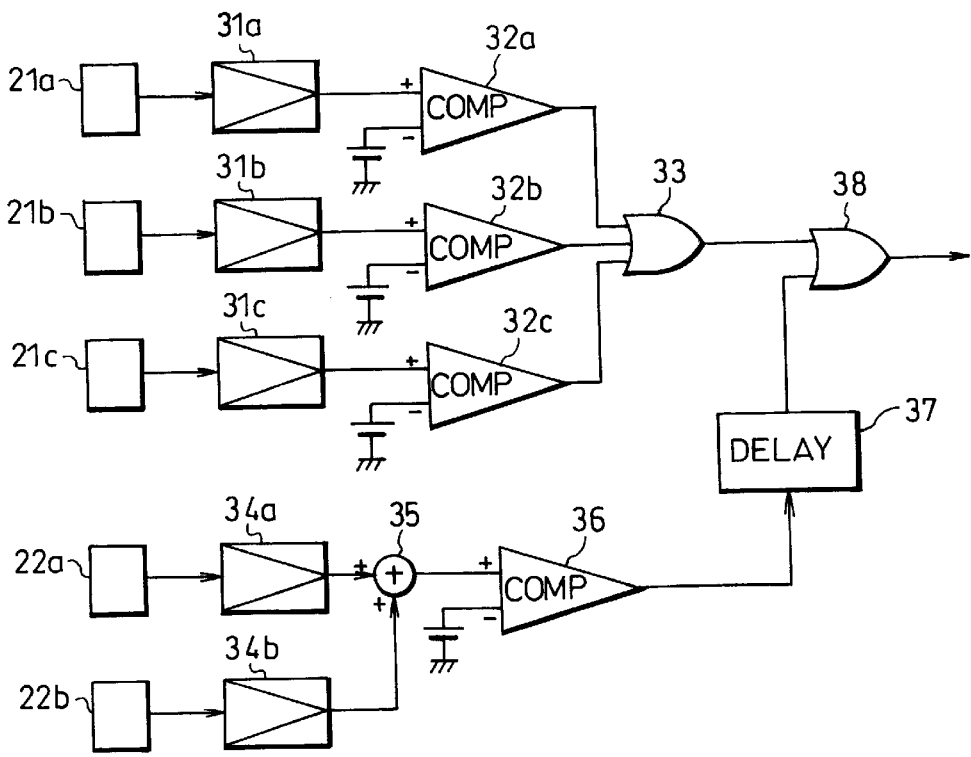

WRAPPING PAPER DEFECT INSPECTION APPARATUS FOR A CIGARETTE MANUFACTURING MACHINE

BACKGROUND OF THE INVENTION

1. Field of the Invention

This invention relates to a wrapping paper defect inspection apparatus incorporated in a cigarette manufacturing machine, and more particularly, to a wrapping paper defect inspection apparatus which is capable of real-time detection of defects, such as pinholes, in elongate wrapping paper continuously supplied to a wrapping section for wrapping shredded tobacco therein and which is suited for rejecting defective cigarettes from among the cigarettes manufactured by cutting a tobacco rod having the shredded tobacco wrapped in the wrapping paper to cigarettes of predetermined length.

2. Description of the Related Art

In a cigarette manufacturing machine, cigarettes are manufactured by feeding shredded tobacco onto elongate wrapping paper continuously supplied to a wrapping section, wrapping the shredded tobacco in the wrapping paper to form a tobacco rod, and then cutting the tobacco rod to cigarettes of predetermined length. Also, a filter is attached to one end of each cigarette cut from the tobacco rod. In this type of cigarette manufacturing machine, the speed of wrapping shredded tobacco shows a tendency to increase.

The quality of wrapping paper affects the flow of air in cigarettes and has an influence upon the combustibility and taste of cigarettes. If, for example, the wrapping paper of a cigarette has a smaller thickness in part thereof or has a pinhole of about 1 mm in diameter therein, the flow of air in the cigarette is liable to change when the cigarette is smoked. To manufacture high-quality cigarettes, therefore, it is necessary that the quality of the wrapping paper be carefully controlled.

The wrapping paper, which is at first in the form of a paper roll and is elongate with a width of about 27 mm, for example, is unrolled to travel at high speed along a predetermined transportation path and is continuously supplied to the shredded tobacco wrapping section of the cigarette manufacturing machine. It is therefore difficult to detect defects in the wrapping paper, such as pinholes, without fail.

Specifically, defects in the wrapping paper need to be detected on a real-time basis while the wrapping paper is caused to travel at a high speed matching the shredded tobacco wrapping speed. However, since the wrapping paper traveling at high speed is liable to sway in the width direction, it is difficult to detect defects such as pinholes with high accuracy. Such sway of the wrapping paper may be suppressed by controlling the supply (travel) of the wrapping paper with high accuracy, but this requires the use of equipment considerably large in scale and complicated in structure.

SUMMARY OF THE INVENTION

One object of this invention is to provide a defect inspection apparatus which permits easy and reliable detection of defects such as pinholes in elongate wrapping paper continuously transported at high speed. Another object of the invention is to provide a cigarette manufacturing machine capable of rejecting without fail cigarettes formed using a defective portion of the wrapping paper, thereby enhancing the quality of manufactured cigarettes.

The above objects are achieved by a wrapping paper defect inspection apparatus according to this invention, and a wrapping paper defect inspection apparatus according to a first aspect of the invention is incorporated in a cigarette manufacturing machine for manufacturing cigarettes by continuously feeding shredded tobacco onto elongate wrapping paper continuously supplied to a wrapping section, wrapping the shredded tobacco in the wrapping paper to form a tobacco rod, and by cutting the tobacco rod to cigarettes of predetermined length.

The wrapping paper defect inspection apparatus according to the first aspect of the invention comprises an optical sensor unit having an optical path crossing a transportation path of the wrapping paper, for receiving, through the wrapping paper traveling along the transportation path, light irradiated onto a region of the wrapping paper excluding edge portions thereof; and a defect determining section for determining whether or not there is a defect in the region of the wrapping paper excluding the edge portions, based on an amount of light received by the optical sensor unit, and for outputting a determination result in synchronism with timing for wrapping the shredded tobacco in the wrapping paper.

A wrapping paper defect inspection apparatus according to a second aspect of this invention comprises, in addition to the elements of the apparatus according to the first aspect of the invention, an auxiliary optical sensor unit having optical paths crossing the transportation path of the wrapping paper, for receiving, through the wrapping paper traveling along the transportation path, light irradiated to regions including the respective edge portions of the wrapping paper; and an auxiliary defect determining section for determining whether or not there is a defect in the edge portions of the wrapping paper, based on a sum of amounts of light received by the auxiliary optical sensor unit, and for outputting a determination result in synchronism with timing for wrapping the shredded tobacco in the wrapping paper.

According to the first aspect of this invention, the defect determining section determines whether or not light has been received, based on the amount of light received by the optical sensor unit, and outputs a determination result that the wrapping paper has a defect including a pinhole therein if it is judged that light has been received. The defect determining section outputs, as a rejection command, the determination result at timing at which a cigarette formed using a detected defective portion of the wrapping paper reaches a predetermined rejection position, to reject the cigarette.

According to the second aspect of this invention, the auxiliary defect determining section outputs a determination result that the wrapping paper has a width smaller than a prescribed width, if the sum of the amounts of light received by the auxiliary optical sensor unit is greater than a predetermined threshold. The auxiliary defect determining section outputs, as a rejection command, the determination result at timing at which a cigarette formed using a narrower portion of the wrapping paper than the prescribed width reaches a predetermined rejection position, to reject the cigarette.

Thus, according to this invention, a defect such as a pinhole is detected using transmission type optical sensors in accordance with whether or not light has passed through the region of the wrapping paper excluding the edge portions thereof, whereby a defect, such as a pinhole, in the wrapping paper transported at high speed can be detected without fail on a real-time basis by using inexpensive optical sensors.

Also, according to this invention, light irradiated to the regions including the respective edge portions of the wrapping paper and not obstructed by the wrapping paper is detected using the auxiliary optical sensor unit, and based on the sum of the amounts of light received by the auxiliary optical sensor unit, a determination as to whether or not the wrapping paper has an improperly small width is made, whereby such a defect can be detected without fail on a real-time basis regardless of sway of the wrapping paper in the width direction accompanying high-speed travel of the paper.

With the above arrangement of the invention, defects in the wrapping paper, such as pinholes or an improperly small paper width, can be easily detected without fail and this detection is not affected by sway of the wrapping paper in the width direction, whereby cigarettes formed using a defective portion of the wrapping paper can be rejected without fail based on the result of detection. Thus, the quality of manufactured cigarettes can be enhanced without sacrificing the wrapping speed of cigarettes.

The above and other objects, features, and advantages of this invention will become apparent from the following description when taken in conjunction with the accompanying drawings.

BRIEF DESCRIPTION OF THE DRAWINGS

FIG. 4A is a diagram illustrating the principle of detection of defects in edge portions of the wrapping paper by means of the auxiliary optical sensor unit, and showing a state in which the wrapping paper is not deviated in the width direction;

FIG. 4B is a diagram illustrating the principle of detection of defects in the edge portions of the wrapping paper by means of the auxiliary optical sensor unit, and showing a state in which the wrapping paper is deviated to the left (upward in the figure) with respect to the traveling direction thereof;

FIG. 4C is a diagram illustrating the principle of detection of defects in the edge portions of the wrapping paper by means of the auxiliary optical sensor unit, and showing a state in which the wrapping paper is deviated to the right (downward in the figure) with respect to the traveling direction thereof;

FIG. 4D is a diagram illustrating the principle of detection of defects in the edge portions of the wrapping paper by means of the auxiliary optical sensor unit, and showing a state in which the wrapping paper has an improperly small width; and FIG. 5 is a diagram showing, by way of example, the arrangement of a defect determining section and an auxiliary defect determining section shown in FIG. 2.

DETAILED DESCRIPTION OF THE PREFERRED EMBODIMENT

A cigarette manufacturing machine and a wrapping paper defect inspection apparatus incorporated therein, according to one embodiment of this invention, will be hereinafter described with reference to the drawings.

Figure 1:
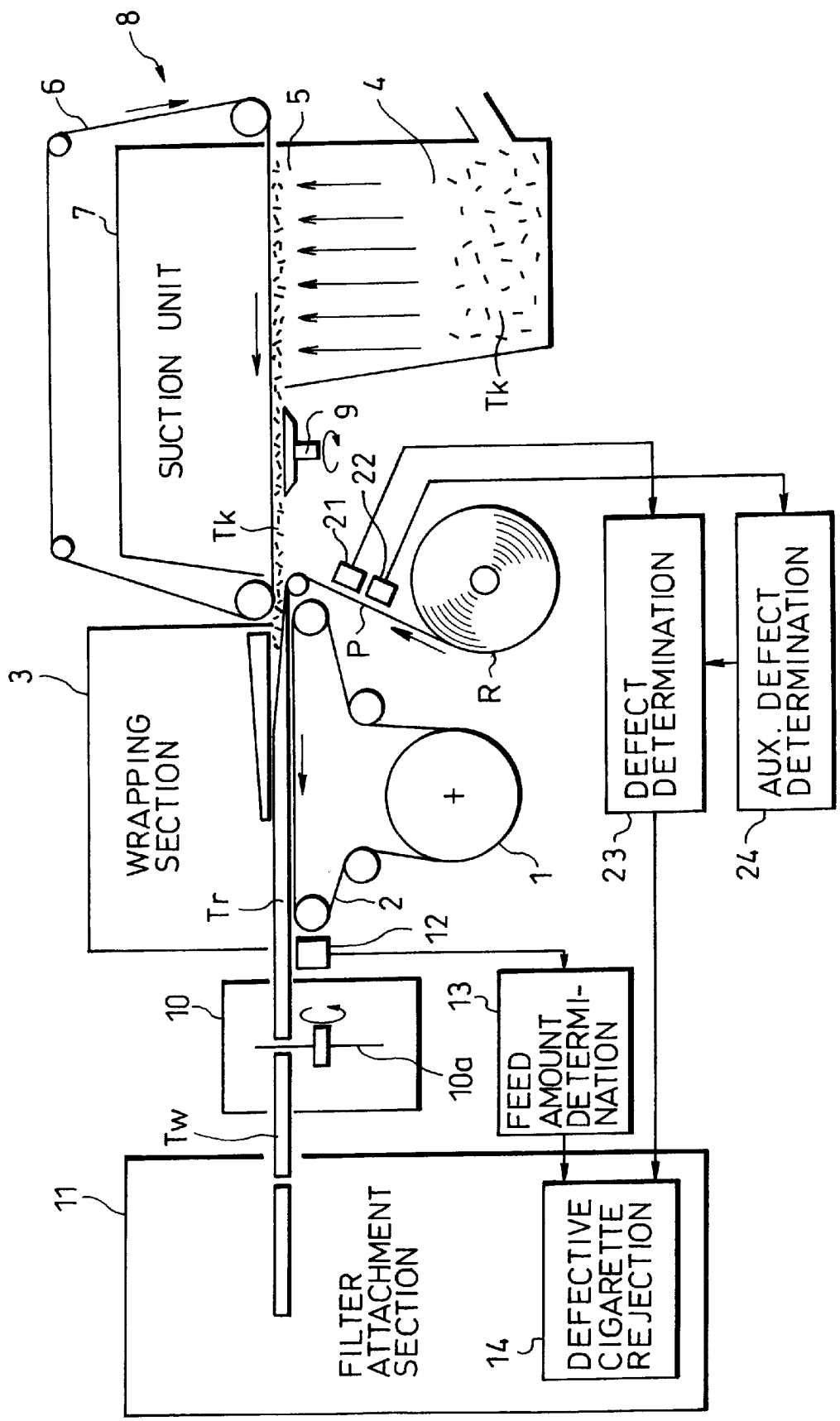
FIG. 1 is a diagram schematically showing the arrangement of a cigarette manufacturing machine.

A cigarette manufacturing machine is, as schematically shown in FIG. 1, provided with a shredded tobacco feeding apparatus 8, a wrapping section 3, and a filter attachment section 11. The wrapping section 3 has a continuous garniture tape 2 which is driven with the speed thereof controlled by a main shaft 1. Elongate wrapping paper P continuously supplied from a paper roll R is transported by the garniture tape 2. The wrapping section 3 continuously wraps shredded tobacco Tk, which is fed onto the wrapping paper P from the shredded tobacco feeding apparatus 8, in the wrapping paper P to form a tobacco rod Tr.

The shredded tobacco feeding apparatus 8, which serves to feed shredded tobacco Tk to the wrapping section 3 as stated above, is equipped with a chimney section 5 for raising by air the shredded tobacco Tk supplied to a hopper 4, and an endless tobacco band 6 passed so as to extend from an upper portion of the chimney section 5 to the wrapping section 3. The tobacco band 6 comprises a belt having a large number of suction holes (not shown) formed uniformly in its entire surface and is driven in a manner synchronized with the rotation of the main shaft 1. The tobacco band 6 attracts the shredded tobacco Tk in layers on a surface thereof with the aid of a negative pressure applied to the other surface thereof by a suction unit 7, and conveys the shredded tobacco Tk to the wrapping section 3.

A trimming disk (écrêter disk) 9 is arranged halfway in the travel path of the tobacco band 6 moving from the chimney section 5 of the shredded tobacco feeding apparatus 8 to the wrapping section 3. The trimming disk 9 operates in synchronism with the rotation of the main shaft 1 and scrapes off a surplus part of the shredded tobacco Tk attracted to the surface of the tobacco band 6 to adjust the layer of the shredded tobacco Tk to a predetermined thickness and thereby control the amount of attracted tobacco (layer thickness). Thus, the amount of the shredded tobacco Tk attracted to the surface of the tobacco band 6 and fed to the wrapping section 3 is controlled by the trimming disk 9. The wrapping section 3 continuously wraps the shredded tobacco Tk, which is thus continuously fed thereto with the feed amount adjusted, in the wrapping paper P to continuously form a single elongate tobacco rod Tr.

The tobacco rod Tr formed continuously in the wrapping section 3 by wrapping the shredded tobacco Tk in the elongate wrapping paper P is cut to parts of predetermined length with a cutting knife 10a of a cutting section 10 arranged next to the outlet of the wrapping section 3. The cutting knife 10a is rotated in accordance with the length of the tobacco rod Tr being formed so that double cigarettes Tw whose length is twice that of a cigarette, for example, may be cut from the tobacco rod Tr. The double cigarettes Tw are then supplied to the filter attachment section 11 and undergo the subsequent process, in which each double cigarette Tw is cut to two equal parts and a filter is attached to one end of each cut part, thereby obtaining filter cigarettes.

A density sensor 12, which comprises a radiation detector, for example, is arranged at the outlet of the wrapping section 3. The sensor 12 continuously detects the filling amount (filling density) of shredded tobacco Tk in the tobacco rod Tr at successive positions thereof in the longitudinal direction. Based on the filling amount of the shredded tobacco Tk detected by the sensor 12, a feed amount determining section 13 monitors, for example, a total filling amount of shredded tobacco Tk corresponding to one cigarette as well as the filling densities of shredded tobacco Tk in the tobacco rod Tr at respective positions thereof in the longitudinal direction, to detect a local excess or deficiency of the shredded tobacco Tk. On detecting a deficiency in the total filling amount of the shredded tobacco Tk corresponding to one cigarette, the feed amount determining section 13 sends a rejection command to a defective cigarette rejecting section 14 provided in the filter attachment section 11, so as to reject a cigarette which is deficient in shredded tobacco and cut from the tobacco rod Tr. Also, the filling densities of the shredded tobacco Tk at respective positions of the tobacco rod Tr in the longitudinal direction, which are monitored by the feed amount determining section 13, are fed back to the trimming disk 9 as a height adjustment signal, so that the feed amount of the shredded tobacco Tk is adjusted in accordance with the signal by the trimming disk 9.

In the cigarette manufacturing machine having the overall arrangement described above, a wrapping paper defect inspection apparatus which characterizes this invention comprises an optical sensor unit arranged halfway in a transportation path along which the wrapping paper P is transported from the roll R toward the wrapping section 3. The defect inspection apparatus generally comprises an optical sensor unit 21 having an optical path crossing the transportation path, and a defect determining section 23 for detecting the presence/absence of a defect in the wrapping paper P based on a change in the amount of light received by the optical sensor unit 21. On detecting a defect such as a pinhole in the wrapping paper P, the defect determining section 23 sends a rejection command to the defective cigarette rejecting section 14 so as to reject a cigarette which is formed using a portion of the wrapping paper P including the defect and which is cut from the tobacco rod Tr.

The defect inspection apparatus is provided, in addition to the optical sensor unit 21 and the defect determining section 23, with an auxiliary optical sensor unit 22 having optical paths crossing the above transportation path, and an auxiliary defect determining section 24 for detecting the presence/absence of a defect in the side edge portions of the wrapping paper P based on a change in the amounts of light received by the auxiliary optical sensor unit 22. On detecting a defective small width of the wrapping paper P caused, for example, due to a cut in an edge thereof, the auxiliary defect determining section 24 sends a rejection command to the defective cigarette rejecting section 14 via the defect determining section 23, so as to reject a cigarette which is formed using a portion of the wrapping paper P including such a defect and which is cut from the tobacco rod Tr.

The optical sensor unit 21 and the auxiliary optical sensor unit 22 each comprise a plurality of line sensortype optical sensors each having a linear sensing area of a predetermined length in the width direction of the wrapping paper P, for example. As seen from FIG. 2 in particular which shows an example of arrangement of the optical sensor units in plan view, the optical sensor unit 21 includes first to third optical sensors 21a, 21b and 21c arranged across the wrapping paper P in the width direction thereof and having an overall sensing area corresponding to a region of the wrapping paper P excluding the edge portions thereof, and the auxiliary optical sensor unit 22 includes fourth and fifth optical sensors 22a and 22b having respective sensing areas so set as to cover the corresponding edge portions of the wrapping paper P.

Figure 3A:
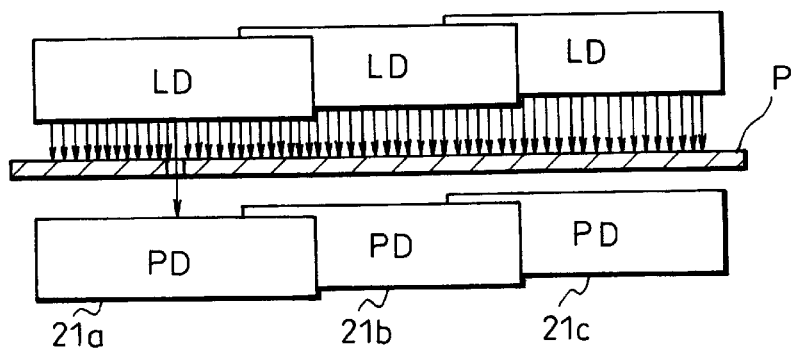
FIG. 3A is a diagram showing the manner of how an optical sensor unit is arranged with respect to wrapping paper.
Figure 3B:
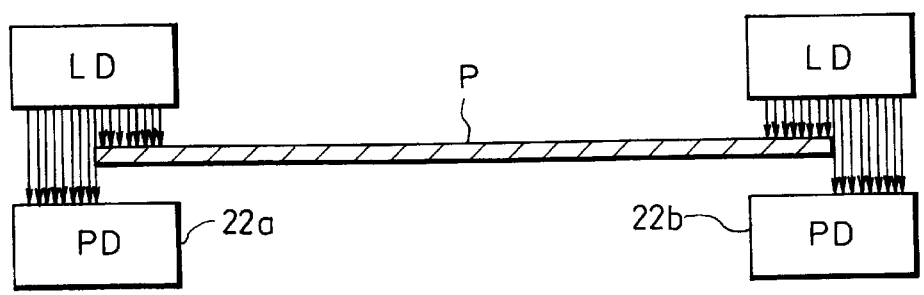
FIG. 3B is a diagram showing the manner of how an auxiliary optical sensor unit is arranged with respect to the wrapping paper.

Each of the optical sensors 21a, 21b, 21c, 22a and 22b has a light-emitting section (semiconductor laser; LD) and a light-receiving section (photodiode; PD) arranged on opposite sides of the wrapping paper P traveling along the transportation path so as to face each other with the wrapping paper P therebetween. Specifically, as shown in FIGS. 3A and 3B, each optical sensor is a transmission type optical sensor for emitting light from the light-emitting section thereof toward the wrapping paper P and for receiving light transmitted through the wrapping paper P by means of the light-receiving section thereof. Thus, a sheet of semiconductor laser light having a predetermined width (e.g., 10 mm) is emitted from each of the optical sensors 21a, 21b, 21c, 22a and 22b, so that linear or slit-like sensing areas are formed on the wrapping paper P across the respective optical paths, thus permitting light that is not blocked by the wrapping paper P to be detected by the light-receiving sections.

Figure 2:
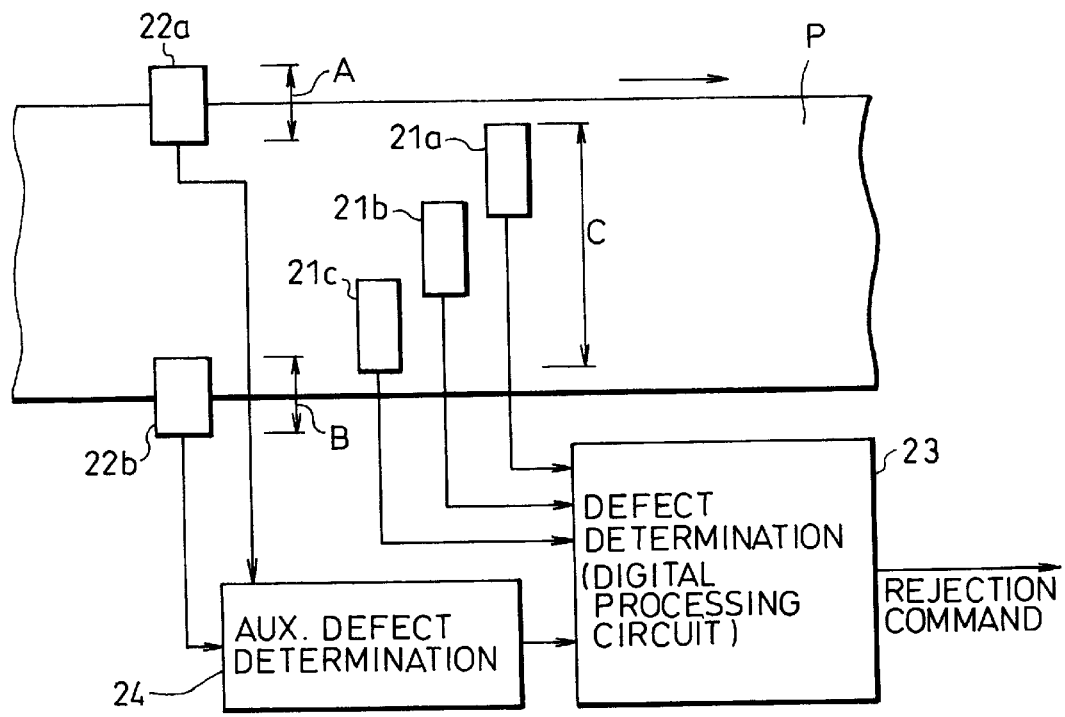
FIG. 2 is a diagram schematically showing the arrangement of a wrapping paper defect inspection apparatus for a cigarette manufacturing machine according to one embodiment of this invention.

The first to third optical sensors 21a, 21b and 21c constituting the optical sensor unit 21 are displaced from one another at a predetermined pitch or distance in the width direction of the wrapping paper P, as shown in FIGS. 2 and 3A, so that the sensing areas of the respective optical sensors 21a, 21b and 21c may be sequentially shifted in the width direction of the wrapping paper P. Namely, the sensing area of each of the optical sensors 21a, 21b and 21c is not large enough to cover the entire width of the wrapping paper P, and therefore, the sensing areas are located close to one another and shifted in the width direction of the wrapping paper P in such a manner that they partly overlap with one another when viewed in the traveling direction of the wrapping paper P.

More specifically, the first to third optical sensors 21a, 21b and 21c are shifted from one another at the predetermined pitch in the width direction of the wrapping paper P so that, when the wrapping paper P is not deviated to one side and is traveling with the center thereof passing exactly on the center of the transportation path, the optical sensors can sense a central region C (width: 25 mm) of the wrapping paper P (total width: 27 mm) excluding the side edge portions thereof (1 mm wide each). Consequently, even in the event that the wrapping paper P deviates to one side approximately by 1 mm due to sway thereof accompanying the transportation, the optical sensor unit 21 can always sense a major surface region of the wrapping paper P without fail.

The fourth and fifth optical sensors 22a and 22b constituting the auxiliary optical sensor unit 22 are located at the same position as viewed in the traveling direction of the wrapping paper P, to sense the corresponding side edge portions of the wrapping paper P. Specifically, the fourth and fifth optical sensors 22a and 22b are each arranged in such a manner that half of their sensing area A, B, for example, covers the corresponding edge portion of the wrapping paper P including the region of 1 mm wide not covered by the optical sensor unit 21. Thus, even if the wrapping paper P deviates to one side approximately by 1 mm due to sway thereof accompanying the transportation, the optical sensors 22a and 22b can sense the respective edge portions of the wrapping paper P without fail.

The light-receiving sections of the first to third optical sensors 21a, 21b and 21c are designed to receive light from the respective light-emitting sections that has passed through the wrapping paper P, and the amounts of light thus received are almost constant, though the light is attenuated while passing through the wrapping paper P. Since the optical sensors 21a, 21b and 21c sense the central region C of the wrapping paper P excluding the edge portions thereof as mentioned above, the amounts of light received by these sensors are almost constant regardless of sway (deviation) of the wrapping paper P in the width direction. If, however, there is a defect in the wrapping paper P, for example, if the wrapping paper P has a smaller thickness in part thereof or has a small pinhole of about 1 mm in diameter therein, the amount of light transmitted through the wrapping paper P increases when such a defective portion passes the sensing area of any of the optical sensors 21a, 21b and 21c.

Each of the optical sensors 21a, 21b and 21c detects such change in the amount of received light, and determines based on a predetermined threshold whether or not the part of the wrapping paper P in the detection area (sensing area) has a defect such as a pinhole therein. The defect determining section 23, which includes a digital processing circuit as its main component, performs an OR operation on the results of detection by the optical sensors 21a, 21b and 21c, to detect without fail a defect, such as a pinhole, in the central region C of the wrapping paper P passing the sensing areas of the optical sensors 21a, 21b and 21c.

On the other hand, the auxiliary defect determining section 24, which includes an analog processing circuit as its main component, adds up the amounts of received light obtained respectively by the fourth and fifth optical sensors 22a and 22b to obtain a sum of the amounts of received light as information indicative of the states of the two edge portions of the wrapping paper P. Then, the sum of the amounts of received light is compared with a predetermined threshold, to thereby determine whether there is a defect or not. Specifically, the optical sensors 22a and 22b for acquiring information about the respective edge portions of the wrapping paper P chiefly receive light that has not been blocked by the edge portions of the wrapping paper P, and the auxiliary defect determining section 24 obtains the sum of the amounts of light received by the optical sensors 22a and 22b.

As schematically shown in FIGS. 4A, 4B and 4C, if the wrapping paper P deviates by Δ in the width direction, the part of light blocked by one edge portion of the wrapping paper P increases while the part of light blocked by the other edge portion correspondingly decreases. Consequently, even if the wrapping paper P deviates in the width direction, the amount of light that is blocked by the two intervening edge portions of the wrapping paper P remains unchanged insofar as the width of the wrapping paper P is constant. In other words, of the two optical sensors 22a and 22b which receive light that is not blocked by the edge portions of the wrapping paper P, one receives a smaller amount of light when the wrapping paper P deviates in the width direction, but the other receives a correspondingly greater amount of light. Consequently, the sum of the amounts Sa and Sb of light received by the respective optical sensors 22a and 22b remains the same regardless of deviation of the wrapping paper P in the width direction, insofar as the wrapping paper P has a constant width with no defect in the edge portions thereof.

If, however, the wrapping paper P has a defect such that it has a smaller width in part thereof as shown in FIG. 4D, then the amount of light blocked by the wrapping paper P correspondingly reduces, causing a change in the amounts Sa and Sb of light received by the optical sensors 22a and 22b. The amounts Sa and Sb of light received by the respective optical sensors 22a and 22b change in the aforementioned manner due to deviation of the wrapping paper P in the width direction. Accordingly, if the amounts Sa and Sb of light received by the optical sensors 22a and 22b are monitored separately from each other, it is not possible to distinguish a change in the amounts of received light caused by a defect in the edge portions of the wrapping paper P, because the amounts Sa and Sb of received light are subject to change due to deviation of the wrapping paper P in the width direction as stated above. However, this invention uses the sum of the amounts Sa and Sb of received light, and since the sum of the amounts of received light remains unchanged insofar as the width of the wrapping paper P is constant, as described above, a reduction in the sum of the amounts of received light can be detected as a change in the amounts of received light caused by a defect in the wrapping paper P.

The auxiliary defect determining section 24, which is based on the principle explained above, compares the sum (Sa+Sb) of the amounts of light received by the fourth and fifth optical sensors 22a and 22b with a predetermined threshold K to thereby determine whether or not there is a defect in the two edge portions of the wrapping paper P. With this arrangement, the detection of such a defect can be effected without being affected by deviation of the wrapping paper P in the width direction accompanying high-speed travel of the paper P. The result of detection by the auxiliary defect determining section 24 is supplied to the defect determining section 23, which then performs an OR operation on the received detection result, like the detection results obtained from the aforementioned optical sensors 21a, 21b and 21c, and outputs a defect detection signal (defective cigarette rejection signal) if a defect is detected.

On detecting a defect in the wrapping paper P in the above-described manner, the defect determining section 23 outputs a defect detection signal to the defective cigarette rejecting section 14 provided in the filter attachment section 11. The output timing of the defect detection signal (rejection signal) for the defective cigarette rejecting section 14 is delayed, based on the time at which the defect in the wrapping paper P is detected by the optical sensor unit 21 or 22, until a cigarette which is formed by wrapping the shredded tobacco Tk in the defective portion of the wrapping paper P and which is cut from the tobacco rod Tr reaches the defective cigarette rejecting section 14. Since the output timing of the defect detection signal (rejection signal) is thus delayed from the defect detection timing, it is possible to selectively reject only a cigarette or cigarettes formed using a defective portion of the wrapping paper, among the cigarettes successively cut from the tobacco rod Tr which is formed by continuously wrapping the shredded tobacco in the elongate wrapping paper P.

The defect determining section 22 and the auxiliary defect determining section 24, which determine whether or not there is a defect in the wrapping paper P on receiving the outputs (amounts of received light) from the first to third optical sensors 21a, 21b and 21c and the fourth and fifth optical sensors 22a and 22b, have an arrangement shown in FIG. 5, for example. Specifically, the defect determining section 22 detects the outputs of the first to third optical sensors 21a, 21b and 21c through respective preamplifiers 31a, 31b and 31c, and makes a comparison between each of the detection outputs and the predetermined threshold in respective comparators 32a, 32b and 32c, to obtain digital signals each indicative of whether or not light has been detected. These digital signals are subjected to OR operation at an OR circuit 33, to thereby determine whether or not light has been detected, that is, whether or not a defect in the wrapping paper P, such as a pinhole, has been detected.

On the other hand, the auxiliary defect determining section 24 detects the outputs of the fourth and fifth optical sensors 22a and 22b through respective preamplifiers 34a and 34b, and adds together the detection outputs in an analog manner by means of an adder 35 to obtain a sum of the amounts of the received light. The output of the adder 35 is compared with the predetermined threshold K at a comparator 36, to thereby determine whether or not there is a defect in the edge portions of the wrapping paper P. A defect detection signal thus output from the comparator 36 is delayed by a delay circuit 37 so that the output timing thereof may be adjusted to the timing of defect detection by the first to third optical sensors 21a, 21b and 21c, and is output through an OR circuit 38 as a rejection signal.

The defect inspection apparatus having the arrangement described above is capable of high-accuracy and high-reliability detection of a defect, such as a small pinhole of about 1 mm in diameter, in the elongate wrapping paper P continuously transported at high speed. In the event that a defect is detected, only a cigarette or cigarettes formed using the defective portion of the wrapping paper can be rejected without fail. Especially in cases where the wrapping paper P travels at high speed to be supplied to the wrapping section 3, defects such as pinholes can be easily detected without fail and this detection is not affected by sway of the wrapping paper P accompanying the high-speed travel, so that cigarettes having a defect in their wrapping paper P can be rejected without fail.

Accordingly, reliable rejection of defective cigarettes can be effected without sacrificing high productivity attained by high-speed wrapping, and the quality of finally produced cigarettes can be effectively enhanced. Further, the function of detecting a defect in the wrapping paper P can be achieved by effective use of general-purpose optical sensors as described above and by the processing circuits with simple arrangement in which the amounts of light received by the optical sensors are compared with the respective predetermined thresholds, and thus practicality of the defect inspection apparatus is extremely high.

This invention is not limited to the foregoing embodiment alone and may be modified in the manners mentioned below. For example, where the optical sensors constituting the optical sensor unit 21 each have a greater sensing area of about 15 mm long, only two optical sensors 21a and 21b may be used for the sensing of the central region C. Where the optical sensor used has an even greater sensing area of about 25 mm long, then the optical sensor unit 21 may be constituted by a single optical sensor. In the foregoing embodiment, transmission type optical sensors are used, but reflection type optical sensors may be used instead. In this case, the reflection type optical sensors are arranged so as to receive light reflected at the surface of the wrapping paper P, and since no light is reflected at a pinhole, such a defect may be detected based on the reflected light. The edge portions of the wrapping paper P are pasted one upon the other and thus are overlapped, and it is very rare that this overlapped region has a pinhole therein; therefore, the detection of a defect in the edge portions of the wrapping paper P may be omitted to thereby simplify the arrangement of the apparatus, especially the wrapping paper defect detecting section. It is to be noted that this invention may be modified in various different ways than mentioned above without departing from the spirit and scope of the invention.

What is claimed is:

1. A wrapping paper defect inspection apparatus incorporated in a cigarette manufacturing machine for manufacturing cigarettes by continuously feeding shredded tobacco onto elongate wrapping paper continuously supplied to a wrapping section, wrapping the shredded tobacco in the wrapping paper to form a tobacco rod, and by cutting the tobacco rod to cigarettes of predetermined length, said wrapping paper defect inspection apparatus comprising:

an optical sensor unit having an optical path crossing a transportation path of the wrapping paper, for receiving, through the wrapping paper traveling along the transportation path, light irradiated onto a region of the wrapping paper excluding edge portions thereof; and a defect determining section for determining whether or not there is a defect in the region of the wrapping paper excluding the edge portions, based on an amount of light received by said optical sensor unit, and for outputting a determination result in synchronism with timing for wrapping the shredded tobacco in the wrapping paper.

2. The wrapping paper defect inspection apparatus according to claim 1, wherein said defect determining section determines whether or not light has been received, based on the amount of light received by said optical sensor unit, and outputs a determination result that the wrapping paper has a defect including a pinhole therein if it is judged that light has been received.

3. The wrapping paper defect inspection apparatus according to claim 1, wherein said defect determining section outputs, as a rejection command, the determination result at timing at which a cigarette formed using a detected defective portion of the wrapping paper reaches a predetermined rejection position, to reject the cigarette.

4. The wrapping paper defect inspection apparatus according to claim 1, further comprising an auxiliary optical sensor unit having optical paths crossing the transportation path of the wrapping paper, for receiving, through the wrapping paper traveling along the transportation path, light irradiated to regions including the respective edge portions of the wrapping paper; and an auxiliary defect determining section for determining whether or not there is a defect in the edge portions of the wrapping paper, based on a sum of amounts of light received by said auxiliary optical sensor unit, and for outputting a determination result in synchronism with timing for wrapping the shredded tobacco in the wrapping paper.

5. The wrapping paper defect inspection apparatus according to claim 4, wherein said auxiliary defect determining section outputs a determination result that the wrapping paper has a width smaller than a prescribed width, if the sum of the amounts of light received by said auxiliary optical sensor unit is greater than a predetermined threshold.

6. The wrapping paper defect inspection apparatus according to claim 4, wherein said auxiliary defect determining section outputs, as a rejection command, the determination result at timing at which a cigarette formed using a narrower portion of the wrapping paper than a prescribed width reaches a predetermined rejection position, to reject the cigarette.

* * * * *